(12) United States Patent
Foss et al.

(10) Patent No.: US 10,213,524 B2
(45) Date of Patent: Feb. 26, 2019

(54) COATING COMPRISING STRONTIUM FOR BODY IMPLANTS

(71) Applicant: ELOS MEDTECH PINOL A/S, Gørløse (DK)

(72) Inventors: Morten Foss, Skanderborg (DK); Ole Zoffmann Andersen, Aarhus C (DK); Michael Brammer Sillassen, Aarhus C (DK); Jørgen Bøttiger, Solbjerg (DK); Inge Hald Andersen, Risskov (DK); Klaus Pagh Almtoft, Solbjerg (DK); Lars Pleth Nielsen, Lystrup (DK); Christian Schärfe Thomsen, Copenhagen N (DK)

(73) Assignee: Elos Medtech Pinol A/S, Gorlose (DK)

( * ) Notice: Subject to any disclaimer, the term of this patent is extended or adjusted under 35 U.S.C. 154(b) by 379 days.

(21) Appl. No.: 14/387,442

(22) PCT Filed: Mar. 22, 2013

(86) PCT No.: PCT/DK2013/050083
§ 371 (c)(1),
(2) Date: Sep. 23, 2014

(87) PCT Pub. No.: WO2013/139345
PCT Pub. Date: Sep. 26, 2013

(65) Prior Publication Data
US 2015/0050618 A1 Feb. 19, 2015

Related U.S. Application Data

(60) Provisional application No. 61/614,798, filed on Mar. 23, 2012.

(30) Foreign Application Priority Data

Mar. 23, 2012 (EP) .................................. 12161072

(51) Int. Cl.
A61C 8/00 (2006.01)
A61L 27/30 (2006.01)
(Continued)

(52) U.S. Cl.
CPC .......... *A61L 27/306* (2013.01); *A61C 8/0015* (2013.01); *A61L 27/30* (2013.01);
(Continued)

(58) Field of Classification Search
CPC .... A61C 8/0012–8/0016; A61K 6/02–6/0235; A61K 6/04; A61K 6/6043;
(Continued)

(56) References Cited

U.S. PATENT DOCUMENTS 6,716,444 B1 * 4/2004 Castro .................. A61L 27/306
424/400
7,910,221 B2 * 3/2011 Contreras ............... A61L 27/06
428/386
(Continued)

FOREIGN PATENT DOCUMENTS

EP 2014319 A1 1/2009
WO 2006004645 A2 1/2006

OTHER PUBLICATIONS

Kung, K.C. et al., "Characteristics and biological responses of novel coatings containing strontium by micro-art oxidation," Surface & Coatings Technology, vol. 205, No. 6, Dec. 15, 2010.
(Continued)

*Primary Examiner* — Garrett K Atkinson
(74) *Attorney, Agent, or Firm* — Klarquist Sparkman, LLP

(57) ABSTRACT

The present invention relates to a coating, a substrate, a method for coating a body and a method for producing the body substrate, such as a dental or a bone implant. The coating has a high degree of mechanical stability and
(Continued)

comprises elements, such as Sr based compounds, which optimize the tissue response to the implanted body thus stimulating healing, bone or tissue growth in the vicinity of the implant. An implant coated with this coating has the ability of sustained release of strontium in a non-toxic concentration of strontium in the vicinity of the implant.

20 Claims, 14 Drawing Sheets

(51) Int. Cl.
    *A61L 27/36* (2006.01)
    *A61L 27/38* (2006.01)
    *A61L 27/56* (2006.01)
    *C23C 14/08* (2006.01)
    *C23C 14/34* (2006.01)

(52) U.S. Cl.
    CPC ........... *A61L 27/303* (2013.01); *A61L 27/365* (2013.01); *A61L 27/3847* (2013.01); *A61L 27/3865* (2013.01); *A61L 27/56* (2013.01); *C23C 14/08* (2013.01); *C23C 14/083* (2013.01); *C23C 14/34* (2013.01); *A61L 2400/12* (2013.01); *A61L 2420/02* (2013.01); *A61L 2420/06* (2013.01); *A61L 2420/08* (2013.01); *A61L 2430/02* (2013.01); *A61L 2430/12* (2013.01); *Y10T 428/24997* (2015.04)

(58) Field of Classification Search
    CPC ........ A61L 27/306; A61L 27/30; A61L 27/56; A61L 27/365; A61L 27/3847; A61L 27/3865; A61L 27/303; A61L 2400/12; A61L 2430/12; A61L 2430/02; A61L 2420/02; A61L 2420/08; A61L 2420/06; C23C 14/083; C23C 14/08; C23C 14/34; Y10T 428/24997
    USPC ...................... 433/167, 191–195, 201.1, 225
    See application file for complete search history.

(56) References Cited

U.S. PATENT DOCUMENTS

| | | | |
|---|---|---|---|
| 7,951,285 B2* | 5/2011 | Zipprish | A61C 8/0012 205/640 |
| 7,998,568 B2* | 8/2011 | Raja | A61L 27/32 205/150 |
| 9,011,965 B2* | 4/2015 | Gan | A61L 27/30 427/2.26 |
| 9,302,030 B2* | 4/2016 | Hossainy | A61L 31/10 |
| 2007/0125247 A1* | 6/2007 | Kunstmann | A61L 27/28 101/170 |
| 2007/0191944 A1* | 8/2007 | Contreras | A61L 27/06 623/11.11 |
| 2007/0202144 A1* | 8/2007 | Hellerbrand | A61B 17/866 424/423 |
| 2007/0202342 A1* | 8/2007 | Whiteford | A01N 43/90 428/425.5 |
| 2008/0237033 A1 | 10/2008 | Misiano et al. | |
| 2009/0082865 A1* | 3/2009 | Raja | A61L 27/32 623/16.11 |
| 2009/0164027 A1* | 6/2009 | Zipprich | A61C 8/0012 623/23.53 |
| 2009/0258327 A1* | 10/2009 | Zipprich | A61C 8/0012 433/173 |
| 2010/0209471 A1 | 8/2010 | Weber | |
| 2011/0045087 A1* | 2/2011 | Kerr | A61N 1/3622 424/490 |
| 2011/0059312 A1* | 3/2011 | Howling | A61L 27/04 428/328 |
| 2011/0143127 A1* | 6/2011 | Gupta | A61L 27/30 428/336 |
| 2011/0251698 A1* | 10/2011 | Gupta | A61F 2/30767 623/23.56 |

OTHER PUBLICATIONS

European Search Report dated Jun. 6, 2013 for PCT Patent Application No. PCT/DK2013/050083.

* cited by examiner

COATING COMPRISING STRONTIUM FOR BODY IMPLANTS

CROSS REFERENCE TO RELATED APPLICATIONS

This application claims the benefit and priority from International Patent Application No. PCT/DK2013/050083, filed Mar. 22, 2013, which claims the benefit and priority from European Patent Application No. 12161072.9, filed Mar. 23, 2012, and U.S. Provisional Patent No. 61/614,798, filed Mar. 23, 2012, each of which are incorporated herein by reference in their entirety and made a part hereof.

FIELD

The present invention relates to a method of coating a body, such as an implant. The invention relates also to a coating for an implant and an implant, such as a dental implant or a bone implant functionalized with elements that optimize the tissue response to implants. The invention further relates to a substrate comprising elements that optimize the tissue response to that substrate and to a method of producing such a substrate.

BACKGROUND

Within dental reconstruction alone, more than 7 million implants are inserted annually, most with good results although more than 3.5% fail, causing pain and discomfort for the patients. Moreover, a majority of the patients experience a prolonged healing period, up to nine months from the insertion of the implant to the crown itself is cemented and the process is complete. During the healing period, the patients experience inferior chewing, dysfunction of the jaw and compromised aesthetics, often with visible lacks and/or obvious temporary solutions.

Titanium is a commonly used implant material in dental and orthopaedic fields due to its inherent biocompatibility originating from, e.g. a high corrosion resistance. In order to obtain mechanically improved Ti implants, alloying elements are typically added. For practical biomedical applications, the alloy TiAl6V4 is the material of choice due to ease of processing. However, one drawback of introducing TiAl6V4 into a biological environment is the potential release of aluminium and vanadium, which are liable to cause harm to human bone tissue, thus degrading the bone integration of the implant.

A way to prevent harmful substances from leaching into biological tissue is by coating the implant alloy with a barrier layer consisting of e.g. pure titanium.

However, the presence of a barrier layer increases the complexity of the implant as well as the cost and time involved in the implant production.

Hence, an improved coating for body implant, such as dental or bone implants, would be advantageous, and in particular a more efficient and/or reliable coating for body implant would be even more advantageous.

OBJECT

It is an object of the present invention to provide a coating for body implant having the ability of healing, reducing the strain and discomfort and lowering the failure rate, proving an enhanced and more painless implantation process to the user.

It is a further object of the present invention to provide a coating for a body implant having a high degree of hardness.

It is a further object of the present invention to provide a coating alternative to the one of the prior arts.

In particular, it may be seen as an object of the present invention to provide a functionalized coating for body implant that solves the above mentioned problems of the prior art with a metal based coating, such as a metal oxide coating.

It is also an object of the present invention to provide a method for producing this coating.

It is a further object of the invention to provide a substrate comprising elements that optimize the tissue response to that substrate.

It is also an object of the present invention to provide a method for producing this substrate.

SUMMARY

Thus, the above described object and several other objects are intended to be obtained in a first aspect of the invention by providing a coating for an implant comprising: a layer comprising strontium oxide, thereby stimulating healing in the vicinity of the implant.

In some embodiments, the layer comprises strontium oxide and titanium oxide, thereby stimulating healing in the vicinity of the implant.

The invention is directed to a coating for an implant and a method of depositing this coating, which optimize the tissue response to the implant, e.g. by stimulating healing, such as tissue healing, in the vicinity of the implant.

When the implant is a bone implant the coating of the invention has also bone growth initiating or stimulating properties. Thus the layer comprising strontium oxide and titanium oxide stimulates bone regeneration in the vicinity of the implant.

When the implant is a dental implant the coating of the invention has also tissue growth initiating or stimulating properties. Thus the layer comprising strontium oxide and titanium oxide stimulates tissue regeneration in the vicinity of the dental implant.

The properties of the implant are due to the ability of sustained release of strontium. The release of strontium may occur in the form of $Sr^{2+}$ ions. Strontium may be toxic when released in high concentration. However they have healing properties, e.g. increase the activity of bone forming cells and improve implant fixation due to stimulated bone regeneration.

The coating of the invention has a structure adapted to achieve a non-toxic release, i.e. release of non-toxic concentration of strontium, e.g. in the form of $Sr^{2+}$ ions, within the implant surroundings, e.g. in the vicinity, such as close vicinity, e.g. within a radius between 0 and 20 mm.

In general when referring to Sr ions release, it may be read within this application also as ions or compounds containing strontium. Thus Sr ions release may be read as release of compounds or ions containing Sr.

Depending on the method of production it may be more appropriate to refer to a substrate than to a coating, for example when the deposition of strontium as metal atom is achieved by ion implantation or ionized physical vapour deposition.

In that the above described object and several other objects are intended to be obtained in a second aspect of the invention by providing a substrate, the substrate having the properties and characteristics of the coating, comprising: a layer comprising strontium oxide and titanium oxide, thereby stimulating healing in the vicinity of the implant.

In a third aspect of the invention an implant comprising a body coated with a coating according to the first aspect of the invention is provided.

In a forth aspect of the invention an implant comprising a body comprising a substrate according to the second aspect of the invention is provided.

In a fifth aspect the invention provides a method of coating a body by means of sputtering, the method comprising: co-depositing from a titanium based target and a strontium based target a layer comprising strontium oxide and titanium oxide onto at least a part of the body.

In a sixth aspect the invention provide a method of coating a body by means of sputtering, the method comprising: co-depositing from a titanium based target and a compound target of a mixture of titanium and SrTiO3 a layer comprising strontium oxide and titanium oxide onto at least one surface of the body.

In a further aspect the invention provide a method for producing a substrate according to the second aspect of the invention.

In general the wording "coating" in relation to the first aspect of the invention can be intended as to be referred also to the wording "substrate" according to the second aspect of the invention. Thus referring to "said coating" through all the text may be also read as "said substrate".

The body referred herein may be an implant such as a dental implant or a bone implant.

Even if the properties of the invention are discussed in relation to the implant to be coated, these may be applied also to in vitro applications. For example in vitro a body, such as e.g. a scaffold, coated with the coating according to the first aspect of the invention or comprising the substrate according the second aspect may release Sr ions locally, thereby stimulating bone regeneration in, e.g. bone tissue contained in vitro. Thus, the invention may be relevant for in vitro applications, e.g. in bone tissue engineering.

In some embodiments the coating of the invention has a structure adapted to achieve a release of strontium ions or ions comprising strontium or strontium atoms or coupound comprising strontium.

In some further embodiments the coating of the invention has a structure adapted to achieve a sustained release of strontium ions or ions comprising Sr atom element or strontium atoms or compound comprising strontium over the initial healing period following the implant. This initial healing period may span up to 3 months.

In some embodiments the coating of the invention has a structure adapted to achieve an accumulated release of strontium ions or ions comprising Sr atom element in a concentration up to 9 µg/cm2.

In some other embodiments the coating of the invention has a structure adapted to achieve an accumulated release of strontium ions or ions comprising Sr atom element in a concentration up to 12 µg/cm2.

In some other embodiments the coating of the invention has a structure adapted to achieve an accumulated release of strontium ions or ions comprising Sr atom element in a concentration up to 20 µg/cm2.

In some further embodiments the coating of the invention has a structure adapted to achieve an accumulated release of strontium ions or ions comprising Sr atom element in a concentration higher than 20 µg/cm2.

In some other embodiment the coating of the invention has a structure adapted to achieve a prolonged release of strontium ions.

The main idea of the invention is to provide a coating for an implant, such as a dental implant having the highest long term release of Sr. This is achieved by combining Sr-content (%), coating thickness and coating porosity so as to achieve the desired release profile of strontium, i.e. the highest long term release.

By being adapted to achieve a slow release rate the coating is therefore adapted to achieve a non-toxic release in the vicinity, e.g. with a radius of 20 mm, of the implant.

Non-toxic is therein defined as a release that does not substantially damage living cells in the vicinity of the implant, i.e. a release in rates where the concentration is lower than the toxic level or tailored to a low toxic level.

Non-toxic release may also be defined as a release that allows absorption of Sr ions by the tissue surrounding the implant in a non-toxic concentration.

The release of strontium ions or ions containing Sr at a slow rate influences the bone homeostasis, e.g. having bone growth initiating or stimulating properties or reducing bone resorption.

For example toxic concentration may be in the order of 40 mg/kg Sr that can cause mortality in mice upon intravenous injection of strontium acetate.

In general $Sr^{2+}$ release increases the activity of bone forming cells, improve implant fixation due to stimulated bone regeneration and reduce bone resorbing activity of osteoclasts.

In some embodiments the layer may comprise titanium oxides having different stoichiometry, e.g. $Ti_xO_y$ such as $TiO_2$, $TiO$ or $Ti_2O_3$.

In some embodiments the layer may comprise strontium oxides having different stoichiometry.

In some embodiments the layer further comprises strontium carbonate.

Generally the method for producing the coating provides a coating without carbon and comprising only Sr, Ti and Oxygen. However through contacts with air, other gases, such as $CO_2$, $O_2$ or $N_2$, may be absorbed at the external surface of the coating and provide external layers only bound at the surface region.

C, O and N elements may also be present in the structure before the exposure to air. The presence of other elements may also be used within the method for producing the coating, e.g. using sputtering targets composed of e.g. titanium and strontium carbonate.

In some further embodiments the layer may comprise strontium salts, such as strontium nitrates or strontium phosphates.

In some further embodiments the layer further comprises metal based compounds. For example the layer may comprise titanium as metal and/or in the form of alloys or salts, e.g. ceramic material such as titanium nitride (TiN), titanium carbon nitride (TiCN) or titanium aluminium nitride (TiAlN).

In some embodiments the coating further comprises an interface layer in between the implant surface to be coated and the layer comprising strontium oxide and titanium oxide.

The interface layer provides a surface with good adhesion properties for the top coating. In general the function of interface layer is to support the coating with good mechanical strength.

In some embodiments the interface layer comprises at least a structured surface. This structured surface may be macro, micro or nano structured and may act as a template in the development of the porosity of the coating.

In some further embodiment the interface layer is a titanium based layer.

For example the interface layer may be a titanium oxide layer.

In some other embodiments the interface layer may be TiN or pure Ti.

Other known interface layers providing good mechanical strength to the top coating layer may also be used.

In some other embodiments the coating further comprises a diffusion layer on top of the layer comprising strontium oxide and titanium oxide.

One of the functions of the diffusion layer is to control or postpone the release of Sr ions. In that a diffusion layer may avoid an initial burst of Sr, which may cause inflammation in the vicinity of the implant, and may ensure a non-toxic release of Sr. In order to avoid this potential initial release of Sr, washing treatment of the implant may be envisaged. This washing may therefore avoid this potential initial release without the need of a diffusion layer. However, washing and presence of diffusion layer may be combined.

A further function of the diffusion layer may be to further diffuse other ions or compounds, such as drugs or medicine included in the mentioned layer or in other layers of the coating.

Another function of the diffusion layer may be to protect the surface for a determined period of time, e.g. hours or days, after the implant has been implanted, before the release of Sr2+ initiates.

The diffusion layer may be for example a polymer layer, such as a biodegradable polymer.

In some further embodiments the coating further comprises a top layer covering the diffusion layer.

In some embodiments the titanium based compounds is in an amorphous and/or crystalline phase.

For example the titanium based compounds may consist of Ti crystalline grains embedded in an amorphous phase.

In some further embodiments the titanium based compounds in the crystalline phase have a grain size below 100 nm.

In some embodiments the titanium grain size is below 50 nm. In some further embodiments the titanium grain size is more preferably between 10 and 50 nm. In some embodiments the titanium grain size is more preferably below 20 nm. In some further embodiments the titanium grain size is even more preferably below 10 nm.

Grain size may refer to the grain cross section.

Generally the co-deposition from a pure Sr target and a pure Ti target has the effect of reducing the size of the titanium nanocrystals in the coating.

The increase of strontium content in the coating increases also the amount of amorphous phase of the titanium. By increasing the strontium content over 12% the coatings are X-ray amorphous.

It has been found that there is a correlation between the strontium content and the coating hardness.

Thus, the coating of the invention may have the advantage of combining a robust and wear resistant structure with the ability of releasing Sr ions in a controlled way, e.g. at a desired rate, having thereby healing and osseo-integration properties in the surroundings of the coated implant.

In some embodiments the Sr-content of the coating is between 0.1 and 50%.

In some embodiments the Sr-content of the coating is between 1 and 40%.

Preferably the Sr-content of the coating is higher than 5%. Even more preferably the Sr-content of the coating is between 0.5 and 15%.

Element content in %, also referred herein as at. %, is defined as the atomic element percentage in relation to the other atomic elements contained in the coating.

The presence of Sr in the coating is therefore characterized in term of % of Sr as atomic element. However, it may be so that Sr is present in the coating not only in the form of oxide but also in other forms such as free ion, i.e. Sr2+, or bound to something else than oxygen or as Sr nano clusters.

In some embodiments the coating has a thickness between 50 and 5000 nm.

In some embodiments the coating has a thickness between 100 and 3000 nm.

Preferably the coating has a thickness of at least 1000 nm. Even more preferably between 1000 and 3000 nm.

In some embodiments the amorphous phase of the coating is between 50 and 90%.

In some other embodiments the amorphous phase of the layer comprising strontium oxide and titanium oxide is between 50 and 90%.

In some further embodiments the crystalline phase of the layer comprising strontium oxide and titanium oxide is between 1 and 50%.

Generally the coating has a structure of nano-crystals embedded in an amorphous matrix.

The coating may have hardness values between 1 to 20 GPa.

In some further embodiments the coating has hardness between 3 to 8 GPa.

More preferable the coating may have hardness values between 5-7 GPa.

The coating hardness may correlate to the coating electron density.

Different values of hardness may be achieved as a function of the coating microstructure.

Optimisation of hardness and Sr release rate may be achieved and implemented by means of computer simulation and/or experimentation.

For example, Sr content for optimal, i.e. desired release may be adjusted so as to obtain a desired hardness. Alternatively Sr content for optimal, i.e. desired hardness may be adjusted so as to obtain a desired release.

The coating may have a certain degree of porosity, e.g. the coating may be meso porous, micro porous or nano porous. The coating may thus have pores having diameters between 0.1 and 100 nm, preferably between 0.1 and 50 nm.

Thus in one aspect the invention provides a coating for an implant comprising: a layer comprising strontium oxide and titanium oxide, wherein the Sr-content of the coating is between 5 and 25%, e.g. between 5 and 20%, such as between 5 and 15% and the thickness of said coating is between 200 nm and 3000 nm, e.g. between 400 and 2600 nm, such as between 600 and 2400 nm, and said coating comprises pores wherein at least 50% of said pores have diameters between 0.1 and 50 nm, e.g. between 2 and 40 nm, such as between 3 and 35 nm, or for example between 0.1 nm and 35 nm, thereby stimulating osseo-integration and healing in the vicinity of the implant.

The porosity of the coating, i.e. the effective surface area may strongly affect the release profile of the strontium and thus in turn the properties of the coating in relation to its effect on the osseo-integration.

In some embodiments the Sr-content of the coating is between 8 and 15% and the thickness of the coating is between 1500 nm and 3000 nm.

In some other embodiments the Sr-content of said the coating is between 8 and 9% and the thickness is between 1400 nm and 1600 nm.

In some further embodiments at least 70% of said pores have a diameters between 0.1 and 50 nm, e.g. between 2 and 40 nm, such as between 3 and 35 nm.

As mentioned above the Sr-content of the coating may be between 0.1 and 50%, e.g. may be up to 30%, and the thickness of the coating between 50 and 5000 nm. However, these intervals combined with a specific porosity has preferred ranges when it comes to producing a coating for an implant aimed at the highest long term release of Sr. This is achieved by combining Sr-content (%), coating thickness and coating porosity so that the coating keeps its mechanical properties allowing for the use as a coating and at the same time achieves the desired released profile of strontium, i.e. the highest long term release.

The desired degree of porosity is preferably achieved by optimizing the deposition method parameters. Preferably the deposition method is physical vapour deposition (PVD). In this case, by depositing under elevated pressure, e.g. between 900 and 1300 mPa, a high degree of porosity, where at least 50% of the pores have diameters between 0.1 and 50 nm can be achieved.

It has been found that the Sr release can be tuned, e.g. increased by variation in the coating deposition, e.g. by increasing the deposition pressure. For example the implants used for the in vivo test has been coated using a pressure range between 450 and 3000 mPa, such as a pressure range between 900 and 1300 mPa, e.g. at 1100 mPa. The porosity of these coatings was higher than the one of the coating performed on other implants where the deposition was performed at 450 mPa or lower.

Thus, Sr release from coating surfaces produced at an increased deposition pressure, relative to the initial tests, i.e. 450 mPa was found to correlate with an increased porosity of the coatings. Hence by increasing the deposition pressure, a higher porosity and thus a more desired Sr release was achieved.

This is however not straightforward as variation in deposition pressure may compromise the mechanical stability of the coating.

The desired porosity may be also achieved by providing a structured surface underneath the coating.

The structured surface maybe a macro, micro or nano structure having the function of a template for the formation of a porous coating.

In search for a coating having the desired mechanical stability and porosity the inventors devised the invention by combining Sr-content (%), coating thickness and coating porosity so as to achieve the desired released profile of strontium, i.e. the highest long term release.

In a further aspect of the invention an implant comprising a body coated with a coating according to the first aspect of the invention by a method of coating according to any other aspect of the invention is provided.

In another aspect the invention provides an implant comprising: a body coated with a layer comprising strontium oxide and titanium oxide, wherein the Sr-content of the coating of the coated body is between 5 and 15% and the thickness of said coating is between 200 nm and 3000 nm, and said coating comprises pores wherein at least 50% of said pores have diameters between 0.1 and 50 nm.

In some embodiments according to the third and further aspects of the invention the body comprises structured surfaces.

In some embodiments according to the third and further aspects of the invention the body comprises metal compounds.

In some embodiments according to the third aspect of the invention the body comprises titanium based compounds. These compounds together with the compounds as previously mentioned may also comprise titanium alloys such as TiAl6V4. In some other embodiments the body comprises other kind of metal alloys, such as Co/Cr or Ni/Cr alloys.

In some further embodiments the body comprises polymers. For example the body may be a thermoplastic polymer, such as Polyether ether ketone (PEEK).

PEEK is a semi-crystalline thermoplastic polymer with excellent mechanical and chemical resistance properties that are retained also at high temperatures and therefore is a good candidate for implants.

Another example of polymer that may be used is Polymethylmethacrylate (PMMA).

In some further embodiments the body comprises composites, such as polymer composites.

In some embodiments the body comprises ceramic material.

Ceramic materials used may be $ZrO_2$ and $MgO$, or bone-like minerals, e.g. $CaCO_3$ and hydroxyapatite.

The coating of the first aspect or the substrate according to the second aspect of the invention may be produced by several methods or combination of methods.

For examples chemical methods such as electrochemical treatments, sol-gel by precipitation from aqueous/non-aqueous solution, and chemical vapour deposition, or physical vapour deposition methods such as sputtering, laser ablation, e-beam evaporation and ion implantation may be used.

Preferably the deposition method is physical vapour deposition (PVD), such as sputtering.

In general, when referring to "sputtering" it may be interpreted as referring to "physical vapour deposition" within the context of the invention.

In particular the substrate according to the second aspect of the invention may be produced by ion implantation.

In a further aspect, the invention provides a method for producing a substrate according to the second aspect of the invention by ion implantation.

Ion implantation of Sr may be achieved by using an ion accelerator, where from an ion source, e.g. $Sr(OH)_2$, Sr or other Sr containing chemical composition, are evaporated and accelerated so as to be implanted. One of the advantages of using Sr implantation for producing the substrate of the invention may be that a better control of the Sr release can be achieved.

The greatest advantage of ion implantation is that the body is not coated but Sr is implanted in the body so that the risk of coating delamination is removed. The basic idea is that the Sr by ion implantation enters deeply into the body substrate. Furthermore, by varying the incoming ion energy, the depth profile of the implanted ions can be finely controlled.

In a further aspect, the invention provides a method of coating an implant by physical vapour deposition techniques, the method comprising: depositing from one or more targets comprising Sr and/or Ti a layer comprising Sr and/or Ti onto at least part of a body.

According to the fourth and further aspects the implant to be coated is introduced into a vacuum chamber, where material is removed from a source, referred to as a target and deposited onto the surface of a body, i.e. the implant, also referred to as substrate.

The way in which materials are removed from the source determines the type of physical vapour deposition used. For example by heating a source in a vacuum setup, deposition onto the substrate may be achieved by thermal evaporation.

In other PVD processes, such as sputtering, atoms are ejected from a source material due to bombardment of the target by energetic particles.

Example of deposition parameters providing the coating and the implant of the invention are:
  pressure between 200 and 2500 mPa;
  temperature between 25 and 550° C.;
  a negative bias voltage between 0 and 110 V applied to the substrate.
Within these ranges the desired coating is produced.

In general titanium based targets and strontium based targets are herein defined as targets comprising titanium and strontium respectively.

In some embodiments according to the fourth and further aspects of the invention the one or more targets comprises $SrTiO_3$.

In some other embodiment the one or more targets comprises $SrX_2$, wherein X is a halogen element.

In some further embodiments the one or more targets comprises $SrCO_3$.

Thus, the targets used may comprise SrO or $SrCl_2$ or $SrF_2$ or $SrCO_3$ or a combination thereof.

Generally Sr targets are not stable in air due to the high reactivity of Sr reacting exothermally with air.

Sputtering from pure Sr target is possible but needs some special requirements from the sputtering system, e.g. a load lock. Thus, with opportune setups sputtering from pure Sr target is achievable.

The method according to the fourth and further aspects of the invention has the unique advantage of using a conductive Sr containing target that is stable in air. In some examples this is achieved by sputtering from a pure Ti target combined with an alloyed/compound target made from a mixture of Ti and $SrTiO_3$.

In some embodiments according to the fourth and further aspects of the invention the method further comprises: depositing a Ti based layer on the body before the deposition step.

In some embodiments according to the fourth and further aspects of the invention the method of coating an implant further comprises: depositing a protective layer after the deposition step.

In a fifth aspect the invention provides a method of coating a body by physical vapour deposition techniques, such as sputtering, the method comprising co-depositing from a titanium based target and a strontium based target a layer comprising strontium oxide and titanium oxide onto at least part of the body.

Co-depositing is referred herein as depositing two different materials from two different sources. Co-depostion of the two different materials may be simultaneous deposition or a deposition of the two different materials delayed in time. Sputtering is referred herein as to a process whereby atoms are ejected from a solid target material due to bombardment of the target by energetic particles, e.g. magnetron sputtering.

In that sputtering covers all types of sputtering methods, such as High Power Impulse Magnetron Sputtering (HiP-IMS) and radio frequency (RF) sputtering, In some embodiments the method according to the fifth aspect of the invention further comprises depositing a Ti based layer on the body before the co-deposition step.

The Ti based layer may be one of the referred to as interface layer in relation to the first aspect of the invention.

In some further embodiments the method according to fifth and other aspects of the invention further comprises depositing a protective layer after depositing the Sr containing layer or the co-deposition step.

In some embodiments according to fifth aspect of the invention the protective layer is a polymer layer.

The protective layer may be referred to herein also as diffusion layer, as disclosed in relation to the third aspect of the invention.

In some embodiments the method according to the fifth aspect of the invention is a method of coating a body according to the third aspect of the invention.

In a sixth aspect the invention provides a method of coating a body by physical vapour deposition techniques, such as sputtering, the method comprising: co-depositing from a titanium based target and a compound target of a mixture of titanium and $SrTiO_3$ a layer comprising strontium oxide and titanium oxide onto at least one surface of the body.

In some embodiments the method according to the sixth and other aspects of the invention further comprises depositing a Ti based layer on the body before depositing the Sr containing layer or the co-deposition step.

The Ti based layer may be one of the referred to as interface layer in relation to the first aspect of the invention.

In some embodiments the method according to the sixth and other aspects of the invention comprises depositing a protective layer after the deposition or the co-deposition step.

The protective layer may be referred to herein also as diffusion layer, as disclosed in relation to the first aspect of the invention.

In some embodiments according to sixth aspect of the invention the protective layer is a polymer layer.

In some embodiments the method according to the sixth aspect of the invention is a method of coating a body according to the third aspect of the invention.

Generally the methods for producing the coating provide a coating without carbon and comprising only Sr, Ti and O. However, upon removal of the coated implant from the deposition chamber, due to contacts with air and other gases, such as $CO_2$, $O_2$ or $N_2$, the adsorption of these gases at the external surface of the coating may produce further layers of Sr/Ti compounds. These layers, because of their formation, i.e. after the deposition step are generally only limited in the external surface region of the coating. These layers may also be formed by reacting with gases introduced into the deposition chamber, during or after the deposition step, before opening the chamber to the atmosphere.

In some embodiments according to any of the aspects of the invention the layer comprising strontium oxide and titanium oxide is a porous layer having pores wherein at least 50% of said pores have a diameter between 0.1 and 50 nm.

In some embodiments according to any of the fourth, fifth, sixth and further aspects of the invention the method of coating an implant comprises contacting the body with an aqueous solution for a period of time between 1 and 120 minutes, preferably between 1 and 60 minutes, more preferably in the range between 20 and 30 minutes, thereby washing the coated body.

In some embodiments according to any of the fourth, fifth and sixth aspects of the invention the method further comprises a pre-treatment before the deposition step, the pretreatment comprising: producing micro or nano structures onto a least one surface of the body.

Implementations of these methods may be directed towards the use of other Sr containing targets having other chemical species such as O, N or C. These species may also be included in the deposition step by using different process gases, e.g. N2, CO2 or O2.

It should however be noted that other known methods for Sr incorporation and deposit formation on an implant surface may also be used in the present invention.

For example Sr may be incorporated by Chemical vapour deposition (CVD), plasma assisted CVD, Thermal CVD, Atomic layer deposition, plasma spraying, reactive sputtering, thermal evaporation, laser ablation, e-beam evaporation or arc-discharge deposition. Alternatively Sr may also be ion implanted into an implant body.

The first, second, third and other aspects of the present invention may each be combined with any of the other aspects. These and other aspects of the invention will be apparent from and elucidated with reference to the embodiments described hereinafter.

BRIEF DESCRIPTION OF THE DRAWINGS

The coating, substrate, implant and methods according to the invention will now be described in more detail with regard to the accompanying figures. The figures show one way of implementing the present invention and is not to be construed as being limiting to other possible embodiments falling within the scope of the attached claim set.

DETAILED DESCRIPTION

Figure 1:
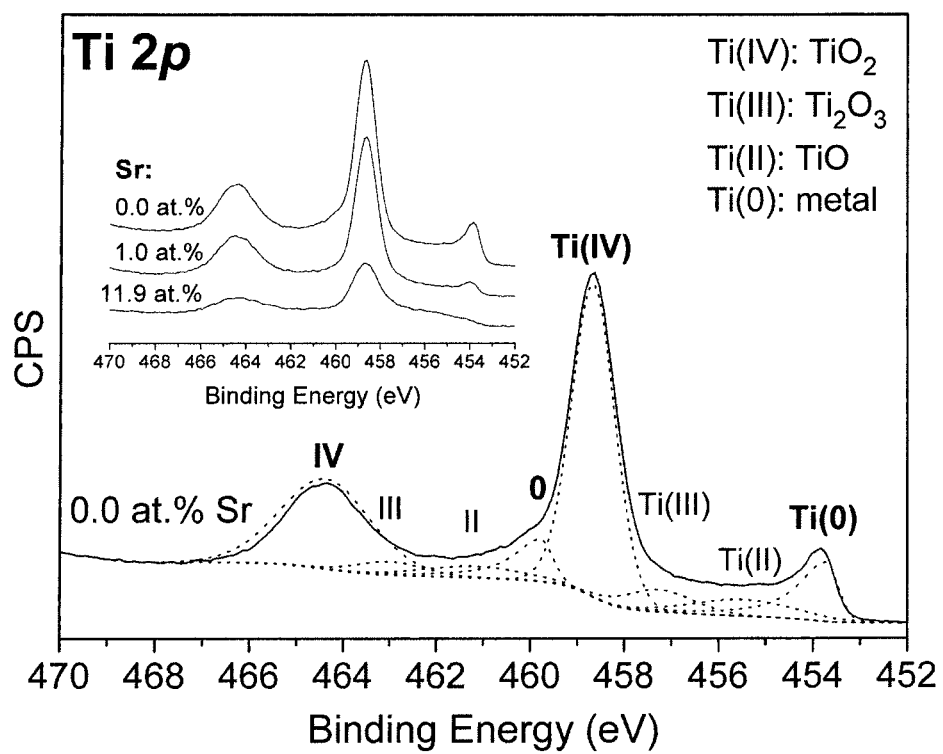
FIG. 1 shows an XPS spectrum of a pure Ti film (main); dotted lines represent the deconvoluted peaks. The inset shows the Ti 2p region from titanium coatings containing 0.0, 1.0 and 11.9 at. % strontium, respectively.

The strontium content in the coating influences the morphology, crystallinity and nanostructure of a sputtered titanium-strontium coating. In particular it appears that strontium reduces the size of the titanium nanocrystals in the coating and that the amount of amorphous material increases with an increasing strontium content. Thus, a coating having a desired level of hardness and where the Sr release rate may be tuned is provided.

EXAMPLE 1

Coating deposited via magnetron sputtering from pure elemental targets.

The coating of the invention may be deposited by means of magnetron sputtering.

For example, depositions were carried out in a high vacuum system with a base pressure of <1×10-5 Pa, using magnetron co-sputtering from 2-inch Ti (99.8%) and Sr (99%) targets. The Ti target was operated in dc power mode, whereas the Sr target was run in current-regulation mode and powered by a bipolar pulsed dc supply (Advanced Energy MDX 1 kW+Sparc-le V unit) in order to remove the naturally formed strontium-oxide layer. During all depositions, the total target power was kept constant at 200 W.

Air pressure-controlled shutters placed between targets and substrate enabled sputter cleaning of the targets prior to deposition. The magnetrons were tilted 25 o away from the substrate normal with a target-to-substrate distance of 20 cm. Depending on the total target power, deposition rates of 4-6 nm/min were obtained at a working pressure of 0.5 Pa with Ar (99.9997%) as inlet gas. The coating thickness was adjusted to ~250 nm by changing the deposition time.

The coating shown in this example is deposited on a Si(001) wafer with native oxide; these substrates were ultrasonically cleaned in acetone and ethanol prior to being inserted into the vacuum chamber. During the depositions, the substrates were electrically floating, and no substrate heating was employed.

However, the coated implants will employ body substrates made of metal, such as Ti based compounds, polymers, e.g. PEEK, or ceramic materials.

The coating thickness was determined from cross-sectional scanning electron microscopy (SEM). The coatings were analysed by X-ray diffraction (XRD). Microstructural information on grain sizes and microstrain was obtained by single-line profile analysis. The electron densities of the coatings were extracted from the respective critical angles obtained from X-ray reflectivity measurements.

The chemical composition of the coating surfaces and the binding structures of the contained elements were analysed by X-ray photoelectron spectroscopy (XPS) operated at an emission current of 10 mA and an accelerating voltage of 15 kV. A charge neutralizer was used to compensate for sample charging. Survey scans were collected from an area of 700×300 μm2 with a pass energy of 160 eV. High-resolution spectra were acquired in the energy region of interest using a pass energy of 20 eV. The high-resolution peaks were deconvoluted using the Gaussian-Lorentzian line shape, GL(30), except for the Ti(0) 2p metal peaks for which an asymmetric line shape, LA(1.1, 5, 7), was used. The respective high-resolution XPS spectra were corrected using a Shirley background. The binding energy scale was calibrated using the C 1s binding energy (285 eV) of adventitious carbon. Prior to XPS analysis, the samples were treated in ultra violet ozone for 30 min., however, no sputter cleaning was performed. The chemical compositions at larger coating depths were obtained through Rutherford backscattering spectroscopy (RBS) using 1.7 MeV 4He+ ions and a scattering angle of 170 o.

Coating hardness values were measured by nanoindentation. For each sample, 64 indents in the load range 100-1000 μN were made. In order to avoid any substrate contribution, the data were cut off at a penetration depth of 50 nm, corresponding to ~20% of the coating thickness. The hardness, H, and the reduced elastic modulus, Er, were determined according to the Oliver-Pharr procedure.

RBS spectra and XPS survey scans revealed Ti, Sr, and O as the main elements in the coating, with C and N (and possibly additionally O) as surface contaminants. RBS analysis revealed that the investigated Ti coatings contained between 0.0 and 11.9 at. % Sr.

Figure 2:
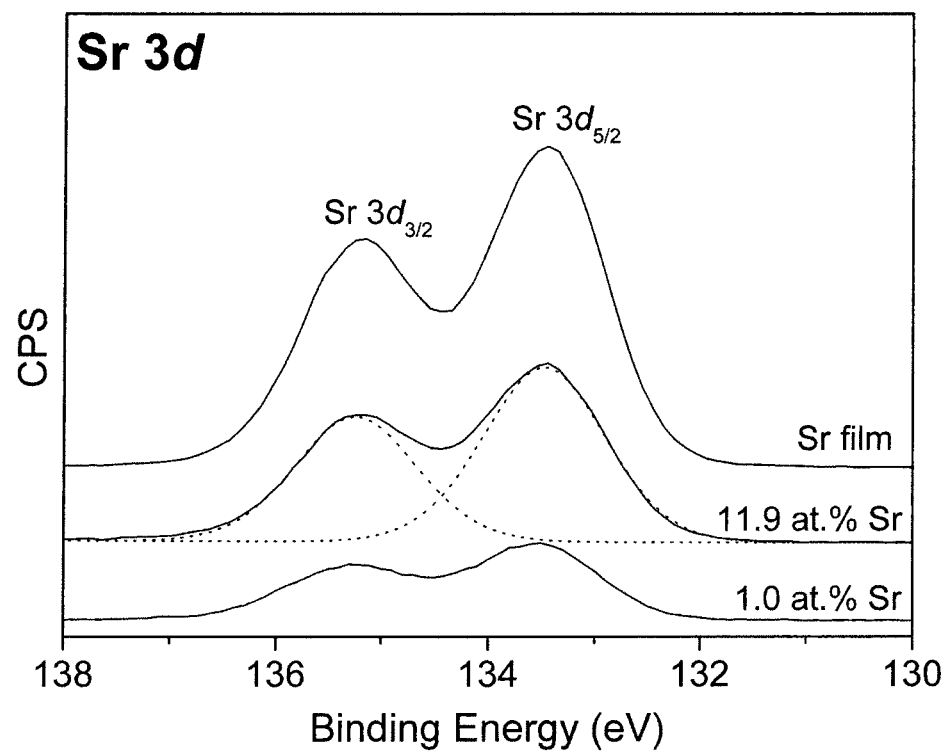
FIG. 2 shows the Sr 3d region from XPS spectra from titanium coatings containing 1.0 and 11.9 at. % of strontium, respectively. A coating containing only Sr is included as a reference. Dotted lines represent the deconvoluted peaks.
Figure 3:
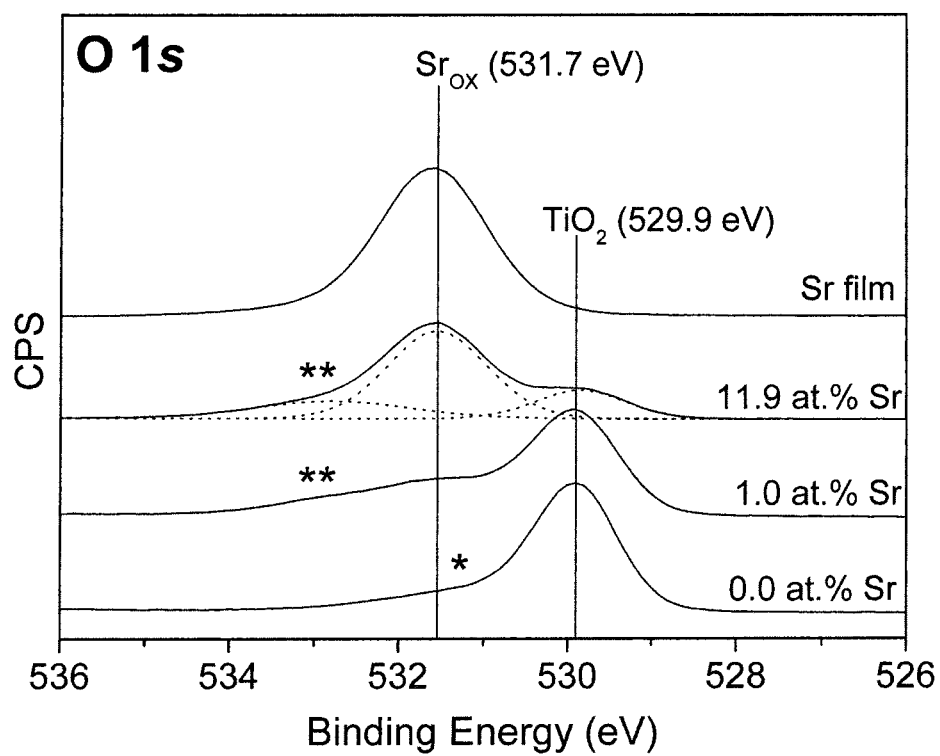
FIG. 3 shows the O 1s region from XPS spectra from titanium coatings containing 0.0, 1.0 and 11.9 at. % of strontium, respectively. A coating containing only Sr is included as a reference. Dotted lines represent the deconvoluted peaks. The superimposed markings denote (*) hydroxylated titanium and (**) physisorbed water, respectively.

FIGS. 1 to 3 show high-resolution XPS spectra of the Ti 2p, the Sr 3d, and the O 1s regions obtained from selected strontium-containing titanium coatings. In FIGS. 2-3, the respective spectra from a fully air-reacted Sr coating have been included for reference. The main part of FIG. 1 shows a spectrum of the Ti 2p region for a pure titanium coating. The included deconvoluted peaks correspond to Ti in various oxidation states. The main contributions are assigned to Ti(IV)O2 and metallic Ti(0), as determined from the peak positions at 458.7 eV (Ti(IV) 2p3/2) and 453.7 eV (Ti(0) 2p3/2) and the corresponding doublet splittings of 5.7 and 6.1 eV, respectively. The inset in FIG. 1 shows the Ti 2p spectra for samples containing 0.0, 1.0, and 11.9 at. % Sr. The Ti 2p peak intensities decrease with increasing Sr content in the coatings. Furthermore, the sample with 11.9 at. % Sr does not exhibit any Ti(0) 2p metal peaks, indicating that a thick oxide top layer has been formed. FIG. 2 shows Sr 3d XPS spectra for samples containing 1.0 and 11.9 at. % Sr, as well as the reference Sr coating (no Ti).

FIG. 3 shows O 1s spectra for samples with strontium contents of 0.0, 1.0, and 11.9%, and the reference strontium coating. Two distinct features are observed from FIG. 3; a peak at 529.9 eV, corresponding to Ti(IV)O2, and a peak at 531.7 eV, which is attributed to strontium-bonded oxygen (Srox). From FIG. 3, a shift from mainly Ti-bonded oxygen for the pure Ti coating to primarily Sr-bonded oxygen for the coating containing 11.9 at. % Sr is observed. From the areas of the deconvoluted peaks (FIG. 3) for the sample containing 11.9 at. % Sr, it is estimated that roughly 60% of the oxygen is associated with strontium in the top surface layer, whereas only 20% is Ti-bonded oxygen. This may explain why the estimated oxygen content increased from ~8 at. % in the pure Ti coating to ~19 at. % in the coating containing 11.9 at. % Sr, since strontium oxidation is generally not confined to the surface region. Moreover, FIGS. 1, 2 and 3 imply that Ti and Sr do not form any mutual bonds.

Figure 4:
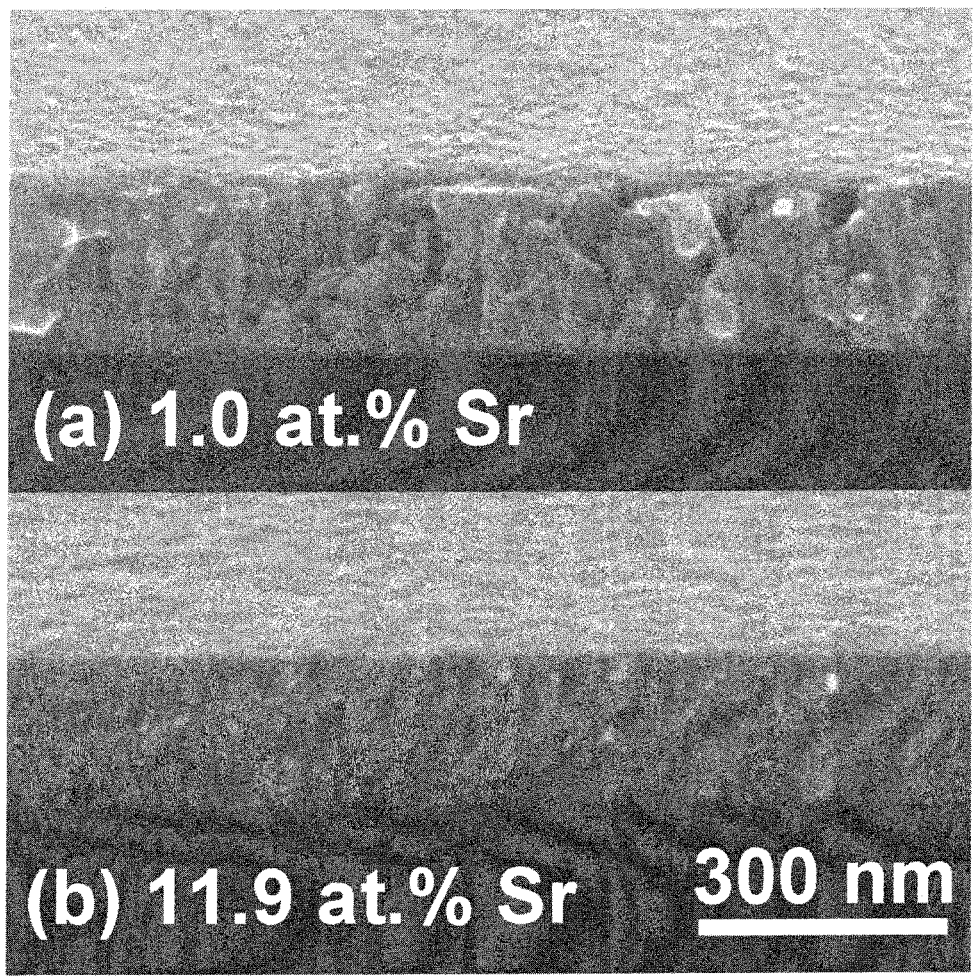
FIG. 4 shows cross-sectional SEM images (tilt angle: 10o) of two coatings with different strontium contents: (a) 1.0 at. % Sr, (b) 11.9 at. % Sr. The scale-bar applies to both images.

FIG. 4 displays SEM images of fractured cross-sections of two coatings with different strontium contents. The coating with 1.0 at. % Sr (FIG. 4a) exhibits a columnar-like morphology resembling that of the pure Ti coating. As can be seen from FIG. 4b, a non-columnar and dense coating morphology is obtained for the sample containing 11.9 at. % Sr.

Figure 5:
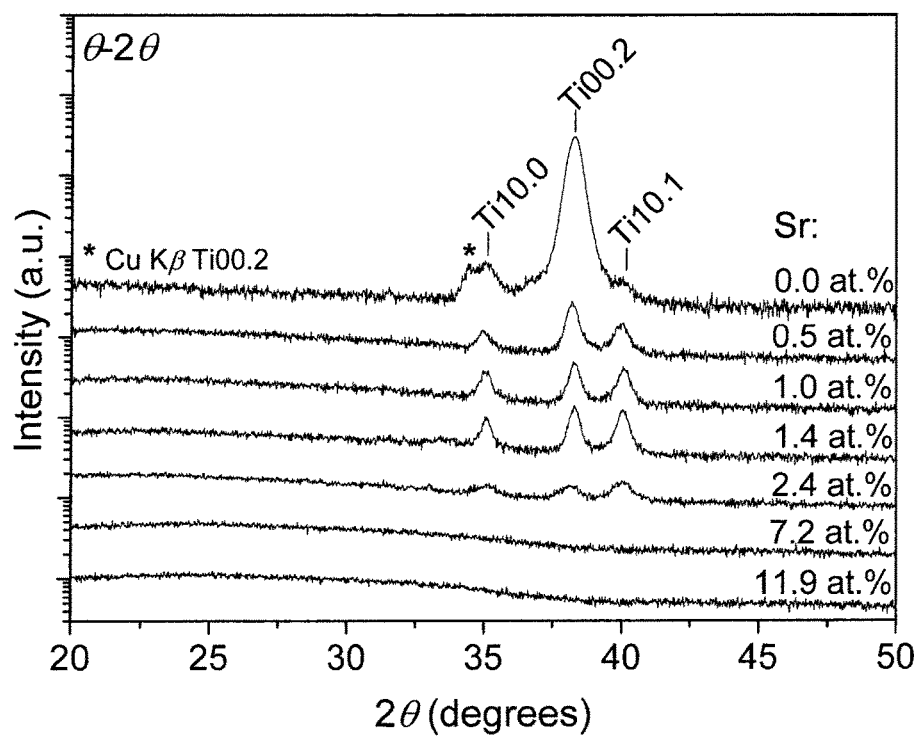
FIG. 5 shows θ-2θ X-ray diffractograms of Ti coatings with Sr contents in the range 0.0-11.9 at. %. The indexed peaks correspond to hcp-titanium. Note that a log-scale is used.

FIG. 5 shows θ-2θ X-ray diffractograms of Ti coatings with strontium concentrations ranging from 0.0-11.9 at. %, as determined from RBS analysis. All peaks can be attributed to hexagonal (hcp) titanium. However, samples with up to 2.4 at. % Sr incorporation have lower crystallinity and a lower degree of preferred orientation as compared to the pure Ti coating. A very broad signal at low 2θ angles emerge and increase as more strontium is incorporated into the coatings. This signal can be interpreted as an amorphous phase surrounding the Ti nanocrystals, with the amount of amorphous material increasing with the Sr content. From FIG. 5, coatings containing 7.2, and 11.9 at. % Sr are observed to be completely X-ray amorphous. An amorphous phase is likely to form during the initial stages of the deposition due to the fact that the concentration of incorporated strontium by far exceeds the solid-solubility equilibrium limit.

Figure 6:
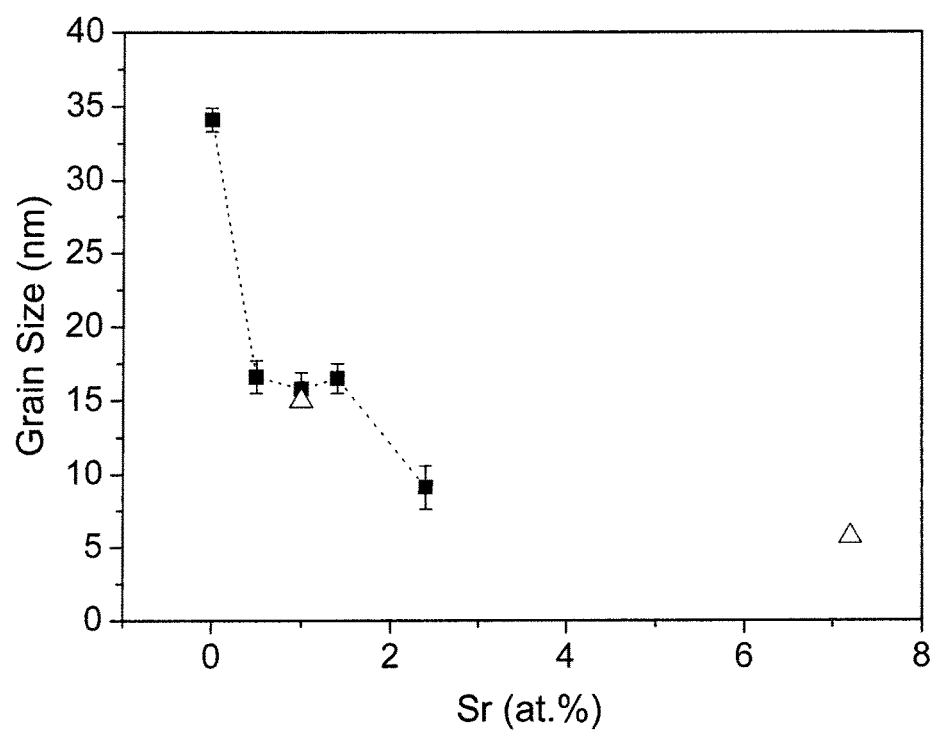
FIG. 6 displays the grain size (closed squares) versus Sr content obtained from the Ti 00.2 diffraction peak. Error bars represent the estimated standard deviations when fitting the X-ray data to a pseudo-Voigt function. Open triangles represent estimated grain sizes from TEM imaging.

FIG. 6 shows the grain size (closed squares) determined from the Ti 002 diffraction peak as shown in FIG. 5 for coatings with strontium contents of 0.0, 0.5, 1.0, 1.4, and 2.4 at. %, respectively. Open triangles represent estimated grain size values from TEM imaging of the samples containing 1.0 at. % Sr (image not shown) and 7.2 at. % Sr. Peak broadening due to microstrain was included in the quantitative analysis of the X-ray data, and the microstrain was observed to decrease from 1.2% in the pure Ti coating to a constant level of ~0.6% in the strontium-containing coatings. From FIG. 7, the Ti grain size is observed to decrease notably from ~34 nm in the pure Ti coating to ~16 nm in the coatings containing 0.5, 1.0, and 1.4 at. % Sr, and to further decrease to ~9 nm in the sample with an Sr content of 2.4 at. %. The average grain size of the X-ray amorphous coating containing 7.2 at. % Sr was estimated to ~6 nm from TEM images. The decrease in the titanium nanocrystal-size with increasing strontium concentrations probably reflects changes in the nucleation and growth rates of nanocrystals precipitated in the amorphous phase.

Figure 7:
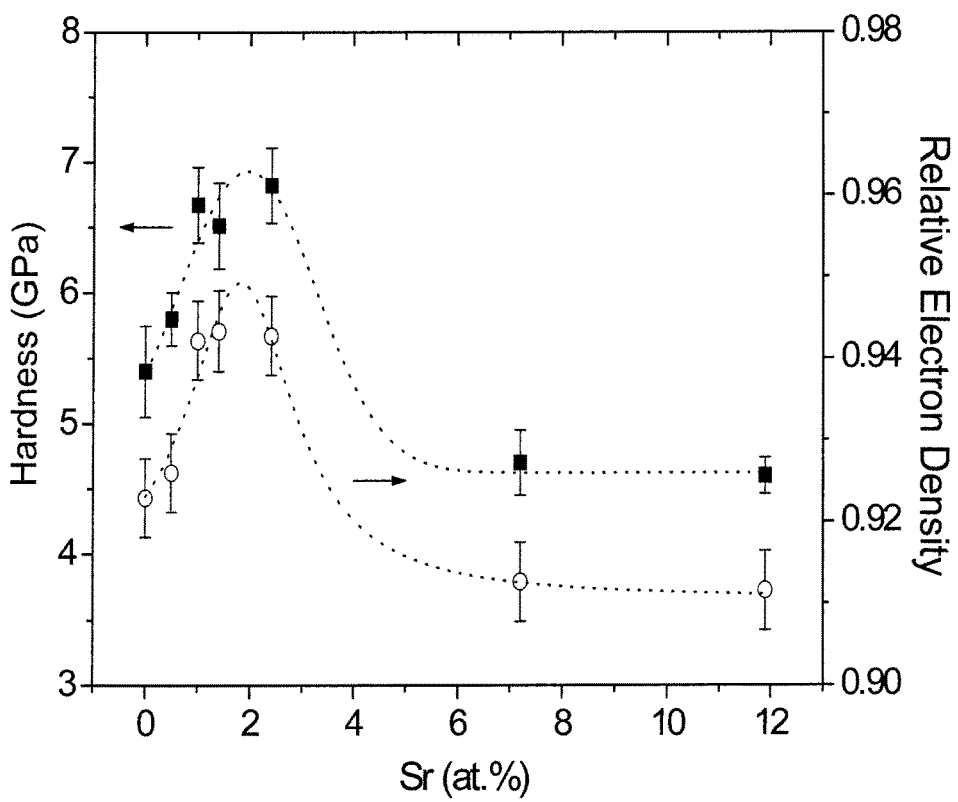
FIG. 7 is a graph plotting coating hardness and relative electron density versus strontium content. Lines are intended as guides for the eye.
Figure 8:
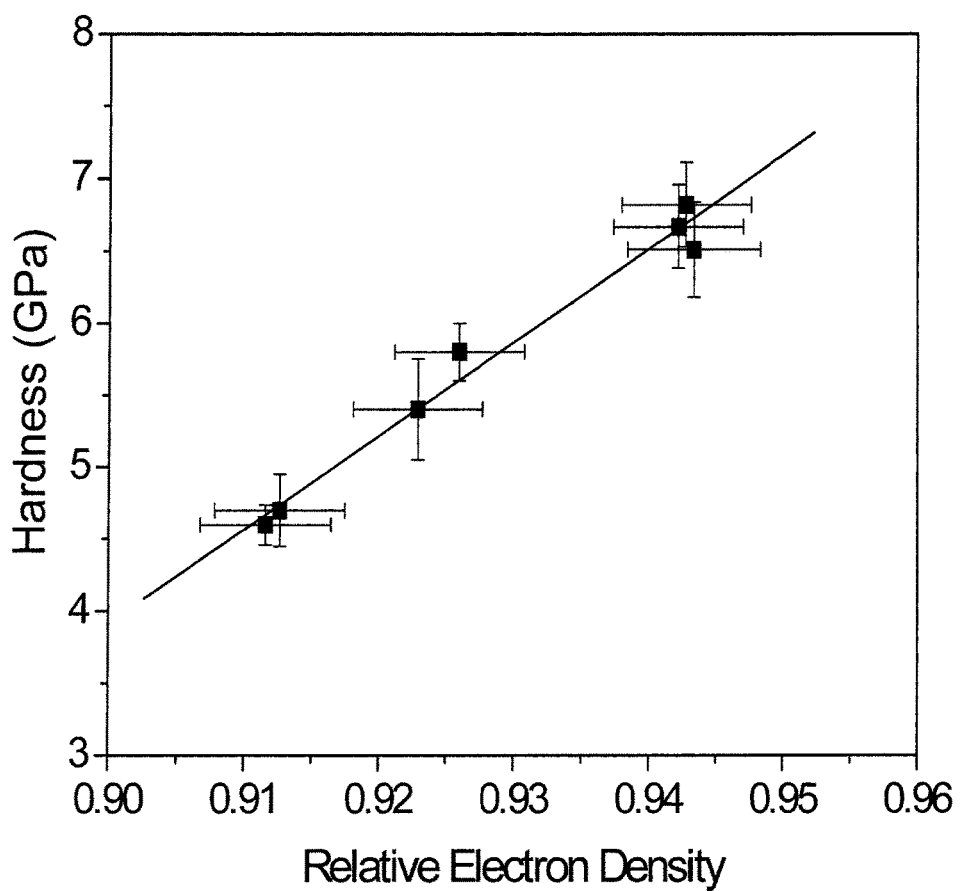
FIG. 8 shows the coating hardness plotted versus relative electron density.

FIG. 7 shows the coating hardness (closed symbols) and the relative electron density (open symbols) as a function of strontium concentration. The relative electron density is here defined as the measured electron density of the coating relative to the tabulated bulk Ti electron density. The coating hardness is observed to increase initially from 5.4 GPa for the pure Ti coating to a maximum value of 6.8 GPa for the coating containing 2.4 at. % Sr. At higher Sr concentrations of 7.2 and 11.9 at. %, the hardness decreases to a constant level of ~4.6 GPa. It is observed from FIG. 7 that the electron density exhibits the same dependence on the Sr content as observed for the hardness. The electron density of the pure Ti coating is ~92% compared to that of bulk Ti. Maximum electron densities corresponding to ~94% of that of bulk Ti are found for the samples containing 1.0, 1.4 and 2.4 at. % Sr. Lower electron densities corresponding to ~91% of that of bulk Ti are observed for the samples with the highest Sr contents of 7.2 and 11.9 at. %. In FIG. 8, the coating hardness is plotted against the relative electron density, showing explicitly that the hardness scales linearly with the electron density.

It appears that the initial density increase, i.e. FIG. 7 reflects the structural and morphological changes due to Sr incorporation into the Ti coatings.

Thus depositions of strontium-containing titanium coatings carried out by magnetron co-sputtering show that the Sr content and the method in which it is deposited influence the resulting nanostructure and morphology as well as the resulting coating hardness and electron density.

This example shows that the amorphous phase in the coatings increases with increasing strontium concentration. Correspondingly, the size of the deposited Ti nanocrystals was observed to decrease with higher Sr concentrations. Furthermore, the coating hardness was observed to scale linearly with the relative electron density. Incorporation of small amounts of Sr by magnetron sputtering resulted in increased electron densities and hardness values.

Figure 9:
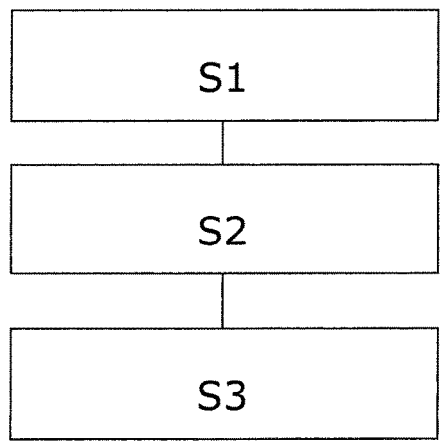
FIG. 9 is a flowchart of a method according to one aspect of the invention.

FIG. 9 is a flow-chart of a method according to one aspect of the invention.

The method of coating a body by means of sputtering comprises the step (S1) of depositing a Ti layer on the body before the deposition or co-deposition step (S2); the step (S2) of depositing or co-depositing from a titanium based target and a strontium based target a layer comprising strontium oxide and titanium oxide onto at least one surface of the body; the step (S3) of depositing a protective layer after the co-deposition step (S2).

Figure 10:
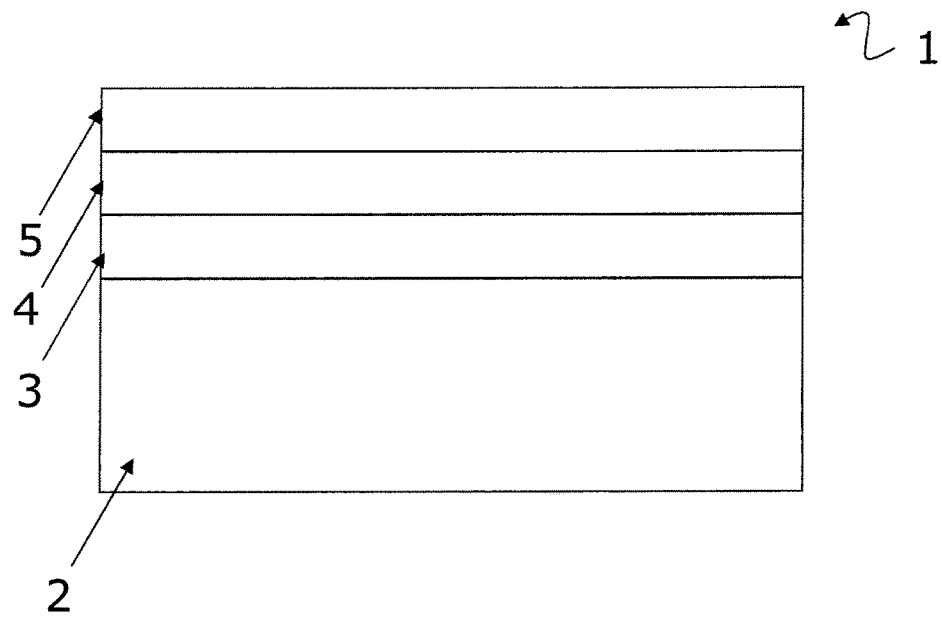
FIG. 10 shows the structure of the coating according to an embodiment of the invention.

FIG. 10 shows the structure of the coating according to an embodiment of the invention.

The coating 1 is shown coating a body 2, such as a Ti implant, with a layer 3 comprising metal based compounds, such as a Ti layer. The functionalizing layer 4 is located on top of the Ti layer. Layer 4 comprises strontium oxide and titanium oxide. An optional protective layer 5, such as a polymer layer may be located on top of layer 4.

Although the present invention has been described in connection with the specified embodiments, it should not be construed as being in any way limited to the presented examples. The scope of the present invention is set out by the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures should also not be construed as limiting the scope of the invention. Furthermore, individual features mentioned in different claims, may possibly be advantageously combined, and the mentioning of these features in different claims does not exclude that a combination of features is not possible and advantageous.

Figure 11:
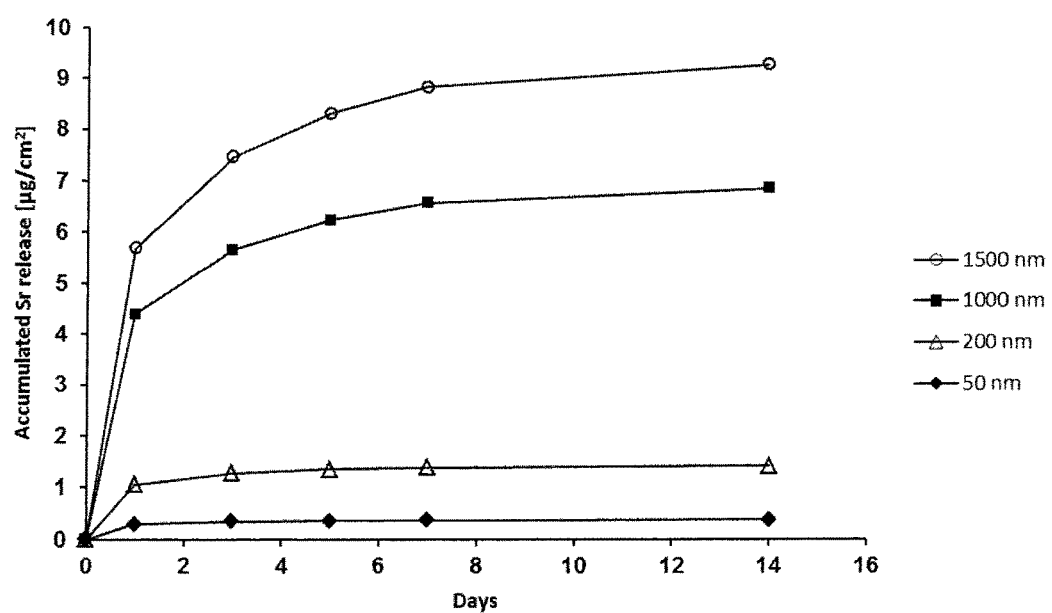
FIG. 11 is a graph plotting the strontium released as measured by using inductively coupled plasma optical emission spectroscopy as a function of time.

FIG. 11 shows the accumulated strontium release as a function of time, as determined via washout experiments. These washout experiments have been carried out on some of the Ti—Sr—O coatings prepared on Grade 4 Ti implant geometries with a diameter of 1.1 mm. The total coated surface area of each implant geometry corresponded to 1 cm2. Briefly, the Sr release was investigated by submerging substrates in Phosphate buffered saline (PBS) using 1 ml/cm2. These were then left for 1 day in an incubator at 37° C. The PBS was then removed and saved for analysis. Then 1 ml/cm2 of fresh PBS was again added to the substrates and left for two more days (day3). At this point the PBS was removed and saved again and fresh PBS was applied to the samples. The last samples were retrieved after a total period of 14 days. The retrieved samples were analyzed using inductively coupled plasma optical emission spectroscopy (ICP-OES). The instrument used for the analysis was an AMETEK Spectro Arcos (AMETEK, Germany). A total of three analyses were performed on each sample and the total amount of sample used for the analysis was approximately 8 ml. It is noticed that the peak value of the strontium release rate can be adjusted and that a prolonged delivery is possible.

Furthermore, FIG. 11 clearly shows that samples having a thicker coating yields the highest long term release of Sr, i.e. ~9 g/cm2 over a period of two weeks. The optimal long term release may be higher than the value measured for the range of samples presented in the figure.

Figure 12:
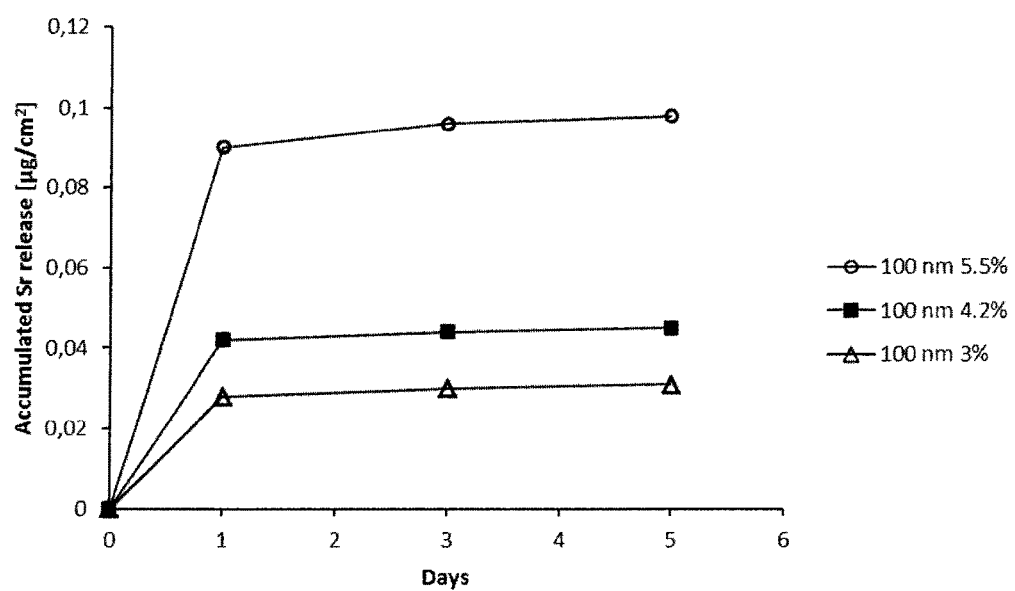
FIG. 12 is a graph plotting the strontium release measured by ICP-OES as a function of time for various elemental compositions (Sr/Ti) of the coatings.

FIG. 12 shows the accumulated strontium release measured by ICP-OES as a function of time for various elemental compositions (at. %) of coatings prepared on silicon wafers. Accumulated Sr release is defined above as the accumulation of the Sr over the release period, thus the data at day 3 correspond to the sum of the data at day 1 and day 3.

These values, such as concentration and release rate may be tuned to desired values through adjustments of the deposition method, Sr concentration, and coating layer structure and thickness.

EXAMPLE 2

Coating deposited for rodent implant.

A total of 40 implants have been tested in 20 rats. 10 of these were reference implants without coating.

The implants had a 1.1 mm diameter and 6 mm length. The coatings deposited on the implants had a Sr concentration of 5.5 at. % and different thicknesses between 50 and 1500 nm.

The implants were fixed to the bone by press-fit, i.e. the only force keeping the implant in place was friction between the implant and the bone.

Figure 13:
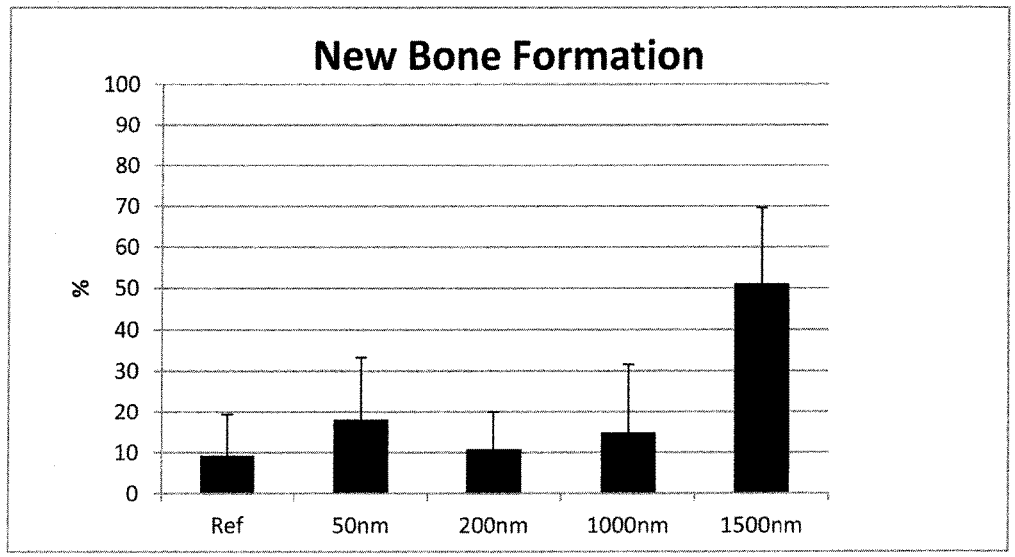
FIGS. 13 and 14 show the outcome of implant test on rats.
Figure 14:
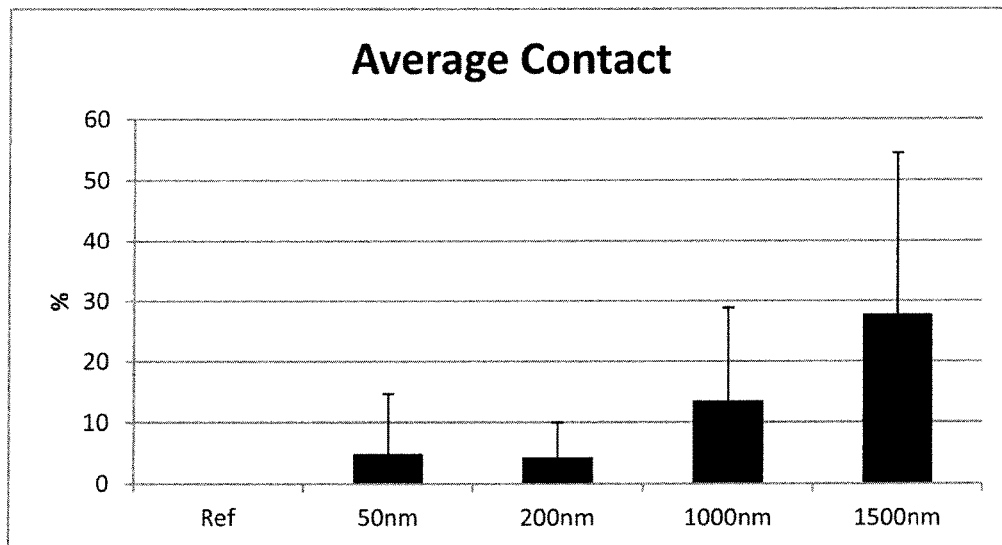

FIGS. 13 and 14 shows the outcome of the test after 4 weeks.

In general it was found that the thickness of the coating increases the surface area, thus an increased surface area appears to be beneficial for the new bone formation. In that it may be possible to achieve similar results with a thinner but more porous coating.

It can also be seen that the presence of the coating increases the bone formation and in particular the presence of a coating of 1500 nm thicknesses achieve a 50% new bone formation.

It can also be seen that an increased average contact between bine and implant was obtained at increased coating thickness corresponding to higher level of Sr release.

EXAMPLE 3

Coating deposited for rodent implant.

A total of 60 implants have been tested in 30 rats.

The implants had a 1.1 mm diameter and 5 mm length. The coatings deposited on the implants had a Sr concentration of 5.5 at. % and 8-9 at. % and a thicknesses of 1500 nm.

The coated implant where exposed to a washout step of 60 or 22 minutes so as to remove eventual segregates of Sr on the surface of the coating. The washout step removes Sr in different forms, e.g. SrO segregated onto the surface, but do not remove the strontium titanate in itself, i.e. the coating in not destroyed. It may be so that during the washout step partial ion exchange may occur.

The implants of this test in vivo employed a slightly different design than the previous test so as to avoid the risk of inflammation due to micro-movements of the implant. The implants used in this in vivo test were shorter, 5 mm instead of 6 mm, and were provided with a thread so as to achieve a better anchorage to the bone.

Figure 15:
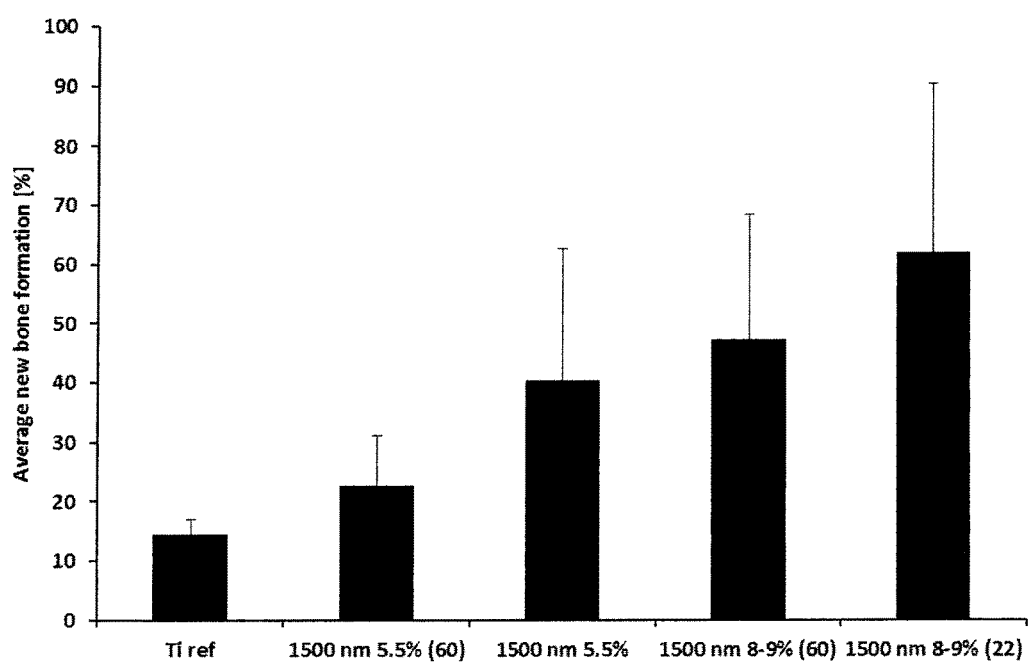
FIGS. 15 and 16 show the outcome of a second implant test on rats after five weeks.
Figure 16:
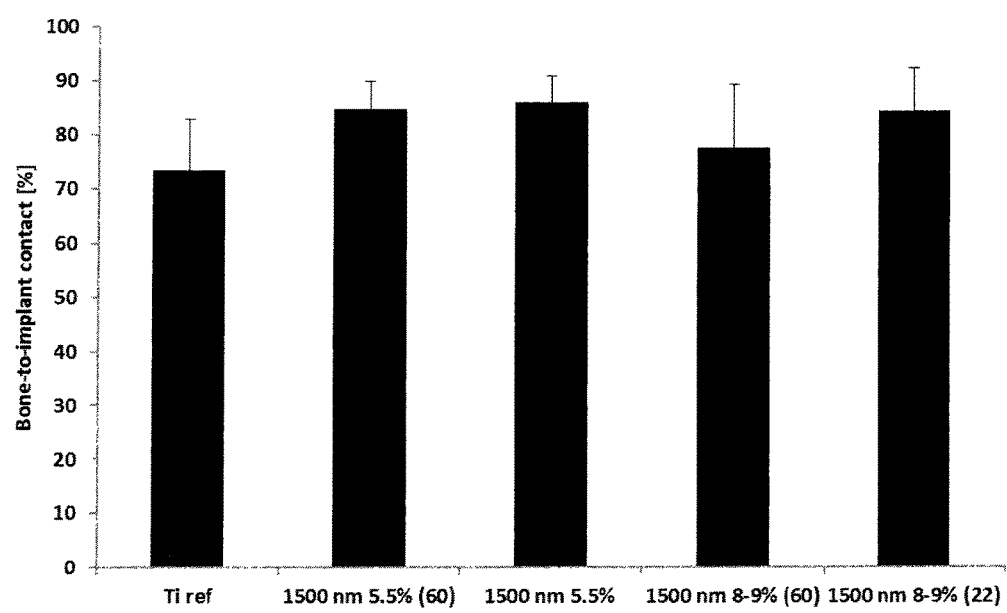

FIGS. 15 and 16 shows the outcome of the second implant test on rats after five weeks.

In search for a coating and therefore an implant where the release of Sr is prolonged in time, i.e. there is a release also after several day from the implantation, thus for a coating allowing for the highest long term release of Sr, it was found that, as it can be noticed from FIG. 15, the coating with the highest concentration, i.e. 8-9% and the lowest washing out time, i.e. 22 minutes, was the one providing the best bone growth and thus the highest release of Sr in the long term according to the expected washout profiles.

FIG. 16 shows the bone-to-implant contact. This is another way to evaluate the growth of bone in the vicinity of the implant. The values reported in FIG. 16 are the bone-to-implant contact % that is the points of contact between the implant and the grown bone after the five weeks implantation period.

In conclusion the results of the tests point towards a coating having a higher Sr concentration and with limited or absence of the washout step.

What is claimed is:

1. A coating for an implant comprising:
    a layer comprising strontium oxide and titanium oxide, wherein the Sr-content of said coating is between 5 and 25 at. % and the thickness of said coating is between 200 nm and 3000 nm, and said coating comprises exposed pores wherein at least 50% of said pores have diameters between 0.1 and 50 nm, thereby stimulating osseo-integration and healing in the vicinity of the implant, wherein the layer is configured to release strontium to support osseo-integration.

2. A coating for an implant according to claim 1, wherein the Sr-content of said the coating is between 8 and 15 at. % and the thickness of said coating is between 1500 nm and 3000 nm.

3. A coating for an implant according claim 1, wherein the Sr-content of said the coating is between 8 and 9 at. % and the thickness is between 1400 nm and 1600 nm.

4. A coating for an implant according claim 1, wherein said layer further comprises strontium carbonate.

5. A coating for an implant according to claim 1, wherein said layer further comprise metal based compounds.

6. A coating for an implant according to claim 1, said coating further comprising an interface layer in between the implant surface to be coated and said layer comprising strontium oxide and titanium oxide, wherein the interface layer comprises a structured surface.

7. A coating for an implant according to claim 6, wherein said interface layer is a titanium based layer.

8. A coating for an implant according to claim 1, said coating further comprising a diffusion layer on top of said layer comprising strontium oxide and titanium oxide.

9. A method of providing a coating for an implant according to claim 1 by physical vapour deposition techniques, the method comprising:
    depositing from one or more targets comprising Sr and/or Ti a layer comprising Sr and/or Ti onto at least part of a body.

10. A method of providing a coating for an implant according to claim 9, wherein said one or more targets comprises $SrTiO_3$.

11. A method of providing a coating for an implant according to claim 9, wherein said one or more targets comprises $SrX_2$, wherein X is a halogen element.

12. A method of providing a coating for an implant by physical vapour deposition techniques according to claim 9, wherein said depositing comprises:
    co-depositing from a titanium based target and a strontium based target a layer comprising strontium oxide and titanium oxide onto at least a part of said body.

13. A method of providing a coating for an implant according to claim 12, wherein said depositing comprises co-depositing from a titanium based target and a compound target of a mixture of titanium and $SrTiO_3$ a layer comprising strontium oxide and titanium oxide onto at least one surface of the body.

14. A method of providing a coating for an implant according to claim 9, the method further comprising:
    depositing a Ti based layer on the body before the deposition step; and
    depositing a protective layer after said deposition step.

15. A method of providing a coating for an implant according to claim 9, further comprising contacting said body with an aqueous solution for a period of time between 1 and 120 minutes, thereby washing said coated body.

16. A method of providing a coating for an implant according to claim 9, further comprising a pre-treatment before the deposition step, said pretreatment comprising:
    producing micro or nano structures onto at least one surface of said body.

17. An implant comprising:
    a body coated with a layer comprising strontium oxide and titanium oxide, wherein the Sr-content of the coating of the coated body is between 5 and 15 at. % and the thickness of said coating is between 200 nm and 3000 nm, and said coating comprises exposed pores wherein at least 50% of said pores have diameters between 0.1 and 50 nm, wherein the layer is configured to release strontium to support osseo-integration.

18. An implant according to claim 17, wherein said body comprises polymers.

19. An implant according to claim 17, wherein said body comprises structured surfaces.

20. An implant according to claim 17, wherein said body comprises ceramic materials.

* * * * *